(12) United States Patent
Brustad et al.

(10) Patent No.: US 7,534,317 B2
(45) Date of Patent: May 19, 2009

(54) KINK-RESISTANT ACCESS SHEATH AND METHOD OF MAKING SAME

(75) Inventors: John R. Brustad, Dana Point, CA (US); Payam Adlparvar, Lake Forest, CA (US); Wassim R. Aliahmad, Irvine, CA (US); Canh T. Tran, Garden Grove, CA (US); Nabil Hilal, Laguna Niguel, CA (US); Boun Pravong, Corona, CA (US); Raffi S. Pinedjian, Fountain Valley, CA (US); Charles C. Hart, Summerville, SC (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 533 days.

(21) Appl. No.: 11/319,870

(22) Filed: Dec. 28, 2005

(65) Prior Publication Data
US 2006/0144501 A1    Jul. 6, 2006

Related U.S. Application Data

(62) Division of application No. 10/298,116, filed on Nov. 15, 2002, now Pat. No. 7,005,026.

(51) Int. Cl.
*B65H 81/00* (2006.01)
*B32B 37/00* (2006.01)
(52) U.S. Cl. ......................... 156/149; 156/171
(58) Field of Classification Search ................. 156/148, 156/149, 171, 169, 173, 175
See application file for complete search history.

(56) References Cited

U.S. PATENT DOCUMENTS

| 2,130,586 A | 9/1938 | Huston |
| 2,688,343 A | 9/1954 | Cuddeback |
| 2,722,263 A | 11/1955 | Beare et al. |
| 3,477,891 A | 11/1969 | Hawerkamp |
| 3,617,415 A | 11/1971 | Hawerkamp |
| 3,910,808 A | 10/1975 | Steward |

(Continued)

FOREIGN PATENT DOCUMENTS

WO    WO 91/12837    9/1991

(Continued)

OTHER PUBLICATIONS

European Patent Office, Supplementary Europeoan Search Report for European Patent Application No. 03796398.0, based on International Application No. PCT/US03/36347 dated Feb. 25, 2009.

*Primary Examiner*—Jeff H Aftergut
(74) *Attorney, Agent, or Firm*—David G. Majdali; Cynthia A. Bonner; Patrick Y. Ikehara (57) ABSTRACT

A method of manufacturing a kink resistant sheath includes the steps of coating a wire with a plastic material to form an inner tube, placing a braid over the inner tube, applying a spring reinforcement over the braid and applying a second layer of plastic material over the assembly to form an outer tube of a braided reinforced sheath. The plastic material is preferably polyurethane but may be a thermoplastic, thermoset or any plastic material having hard and/or soft durometer.

11 Claims, 7 Drawing Sheets

U.S. PATENT DOCUMENTS

| | | |
|---|---|---|
| 3,919,026 A | 11/1975 | Mizutani et al. |
| 3,988,190 A | 10/1976 | McWilliams |
| 4,010,054 A | 3/1977 | Bradt |
| 4,078,957 A | 3/1978 | Bradt |
| 4,135,869 A | 1/1979 | Loyer |
| 4,302,261 A | 11/1981 | Simkins et al. |
| 4,343,672 A | 8/1982 | Kanao |
| 4,350,547 A | 9/1982 | Kanao |
| 4,466,854 A | 8/1984 | Hawerkamp |
| 4,540,360 A | 9/1985 | Leo |
| 4,690,175 A | 9/1987 | Ouchi et al. |
| 4,826,423 A | 5/1989 | Kemp et al. |
| 5,092,950 A | 3/1992 | Spoo et al. |
| H1261 H | 12/1993 | Gibson et al. |
| 5,472,435 A | 12/1995 | Sutton |
| 5,637,168 A | 6/1997 | Carlson |
| 5,836,925 A * | 11/1998 | Soltesz ............ 604/264 |
| 5,846,251 A | 12/1998 | Hart |
| 5,863,366 A | 1/1999 | Snow |
| 5,888,436 A * | 3/1999 | Keith et al. ............ 264/103 |
| 5,971,938 A | 10/1999 | Hart et al. |
| 6,143,013 A * | 11/2000 | Samson et al. ............ 604/264 |
| 6,213,995 B1 * | 4/2001 | Steen et al. ............ 604/527 |
| 6,306,235 B1 | 10/2001 | Henderson |
| 6,368,316 B1 | 4/2002 | Jansen et al. |
| 6,451,005 B1 | 9/2002 | Saitou et al. |
| 6,471,684 B2 | 10/2002 | Dulak et al. |
| 6,537,405 B1 | 3/2003 | Henderson et al. |
| 6,605,171 B1 | 8/2003 | Debalme et al. |
| 2004/0010243 A1 | 1/2004 | Klint |
| 2005/0131387 A1 | 6/2005 | Pursley |

FOREIGN PATENT DOCUMENTS

| | | |
|---|---|---|
| WO | WO 93/15785 A-1 | 8/1993 |
| WO | WO 93/15872 A1 | 8/1993 |

* cited by examiner

KINK-RESISTANT ACCESS SHEATH AND METHOD OF MAKING SAME

This application is a divisional application of U.S. patent application Ser. No. 10/298,116, filed Nov. 15, 2002, now U.S. Pat. No. 7,005,026, the disclosure of which is hereby incorporated by reference as if set in full herein.

BACKGROUND OF THE INVENTION

1. Field of the Invention

This invention generally relates to medical devices and, more specifically, to kink-resistant surgical access devices adapted to introduce surgical instrumentation into body conduits and methods of making same.

2. Discussion of Related Art

Surgical access devices such as sheaths and catheters have long been used to access body conduits. Surgical access devices typically include an access sheath and an obturator or dilator inserted therethrough to facilitate introduction of the access sheath into a body conduit. Once the sheath is positioned inside the body conduit, the obturator is removed leaving a working channel for fluid delivery, fluid recovery, implant delivery and, on many occasions, they provide an access pathway for an instrument such as an endoscope. It follows that such a sheath needs to be as durable and flexible as possible. A serious problem arises when an access sheath is bent or twisted causing the sheath to kink. A kinked sheath is useless because it cannot communicate and because it will not allow the passage of an instrument such as a guidewire or an endoscope. In addition, a kinked sheath may allow an endoscope or other device to puncture the wall. This could present a danger to the body conduit into which the sheath has been inserted. Consequently, the kinked sheath must be removed and/or replaced. As such, there has been a need in the art for an access sheath having a kink-resistant construction. U.S. Pat. No. 5,380,304 (the '304 patent) and U.S. Pat. No. 5,700,253 (the '253 patent) attempt to address the kinking problem by disclosing a sheath comprising an inner tube, a flat wire coil compression fitted around the inner tube, and an outer tube connected to the inner tube through the spacings between the wire coil. Specifically, the outer surface of the inner tube is chemically etched to form a rough outer surface to which the outer tube is mechanically connected using a heat shrinking and formation process. There is still a need, however, for alternative and improved methods of manufacturing kink-resistant sheaths for use in body conduits that are effective, cost-efficient and provide good yields.

Furthermore, the present access sheath has been provided in the form of an elongate tube that has tended to migrate distally and, in some cases, have disappeared beneath the body conduit such as the urethral meatus. U.S. patent application Ser. No. 09/882,630 (Publication No. 2002/0038115 A1), which is hereby incorporated by reference, addresses this problem by providing an access sheath having an enlargement at the proximal end to prevent migration and to facilitate the insertion and removal of instrumentation. In particular, the sheath includes a handle structure at the proximal end that is sized and shaped to accommodate engagement by a user's hand disposed in its natural position with the palm facing the user. Specifically, the handle has a funnel structure that facilitates the introduction of instrumentation into the working channel of the sheath. As a result, the sheath is positioned in a relatively stationary orientation during the insertion and removal of instrumentation. However, these sheaths with handle structures at the proximal ends have large openings and, therefore, it would be desirable to provide a mechanism such as a cap that releasably attaches to the handle structure to further facilitate use with the surgical instruments.

SUMMARY OF THE INVENTION

The present invention is directed to a releasable mechanism such as a cap adapted for use with an access sheath having an elongate tube and a handle structure disposed at a proximal end of the tube, the handle structure extending radially outwardly of the tube forming a funnel with an opening leading into a lumen of the tube. The releasable mechanism is sized and configured to fit the opening of the funnel of the handle structure, which is shaped like the bell of a horn, to further facilitate use with surgical instrumentation. The releasable mechanism may operate as a separate cap that snaps onto the handle structure to provide access pathways to the sheath or prevent passage of fluids or instrumentation into the sheath. The releasable mechanism may also be disposed at a proximal end of a surgical instrument to be introduced into the access sheath such that it may be interlocked with the sheath. The releasable mechanism may include additional openings that provide additional working channels into the sheath.

In a first method of manufacturing a kink-resistant sheath of the invention, a wire is initially coated with a plastic material, the coated wire is then wrapped around a mandrel forming a plurality of windings, and the wound coated wire is heated until the plastic material melts and bonds the windings to form a wire-reinforced sheath. The plastic material is preferably polyurethane but may be a thermoplastic, thermoset or any plastic material having hard and/or soft durometer. The wound coated wire may be heated by capturing the windings within a shrink tube or compressing the windings in a mold and heating the windings until the sheath is formed. In another method of the invention, a wire is alternatively wound around a mandrel in a multifilar fashion with a filament comprising a material different from the plastic coating of the wire. In yet another embodiment of the invention, a hard plastic/soft plastic multifilar is wound around a mandrel in place of the coated wire.

In another aspect of the invention, a mandrel is used as part of an extrusion process. In this process of manufacturing a kink-resistant sheath, the mandrel is coated with a first layer of plastic material to form an inner tube, a spring reinforcement is then placed over the inner tube, which is then coated with a second layer of plastic material to form an outer tube of the sheath. The inner tube and outer tube may be formed by either extrusion or molding. The spring reinforcement may be a pre-wound wire or a wire wound around the inner tube. The material of the wire, the hardness of the wire, the pitch of the windings and the shape of the wire could vary depending on the application of the sheath. The wire, e.g., may comprise a metallic and/or plastic material. In addition, the wire may be round, rectangular, hexagonal or any other shape that facilitates interlocking of the windings.

In another aspect of the invention, another coating or outside layer could be placed over the spring reinforcement in a dipping process. In particular, after the mandrel has been coated and the spring reinforcement has been placed or wrapped, the spring reinforcement is then dipped in a solvent based solution to form the outer layer of the sheath. This final coating could be formed on the sheath using a dipping process either in place of or in addition to the outer layer formed by extrusion. That is, the final coating could be extruded and/or dipped. In yet another embodiment of the invention, a braid such as a polyester braid may be used instead of or in addition to the coil spring to form a kink-resistant sheath. The braid may comprise of woven fibers made of plastic, metal or any combination of plastics and metals. The braid may be heat fused to prevent axial stretching. Furthermore, the braid may be insert molded, fused or bonded onto the sheath.

These and other features and advantages of the invention will become more apparent with a description of preferred embodiments and reference to the associated drawings.

DESCRIPTION OF PREFERRED EMBODIMENTS AND BEST MODE OF THE INVENTION

Figure 1:
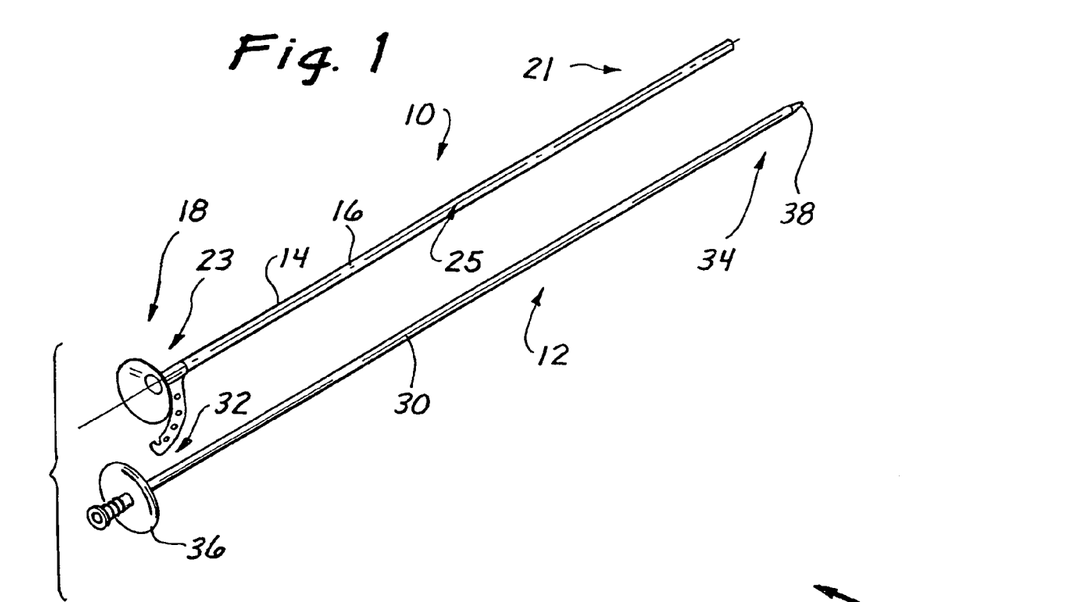
FIG. 1 is a perspective view illustrating a sheath having a handle with an obturator having a releasable mechanism adapted for use with the handle of the sheath.

An access sheath is illustrated in FIG. 1 and is designated generally by reference numeral 10. In FIG. 1, the sheath 10 is illustrated in combination with a separate, but associated, dilator or obturator 12. The sheath 10 has the general configuration of an elongate tube 14 having an axis 16 which extends between a proximal end 18 and a distal end 21. A handle 23 is disposed at the proximal end 18 of the tube 14 and provides access into a working channel 25 of the tube 14. The handle 23 is formed as a radial enlargement having a distally-facing surface and a proximally-facing surface. The distally-facing surface has a generally concave configuration which provides a gradual enlargement inhibiting migration of the sheath 10 into a body cavity such as the ureter. The concave configuration is sized to receive adjacent fingers of a user's hand disposed in its natural position, in order to facilitate the stationary orientation of the sheath 10. The proximal-facing surface has a generally convex configuration providing for an increased funneling of an instrument as it is inserted into the working channel 25 of sheath 10. Thus, the handle 23 has the general configuration of the bell of a horn. This configuration is not only ergonomically comfortable, but also highly practical in addressing the problems of migration, as well as instrument insertion and removal.

Figure 2:
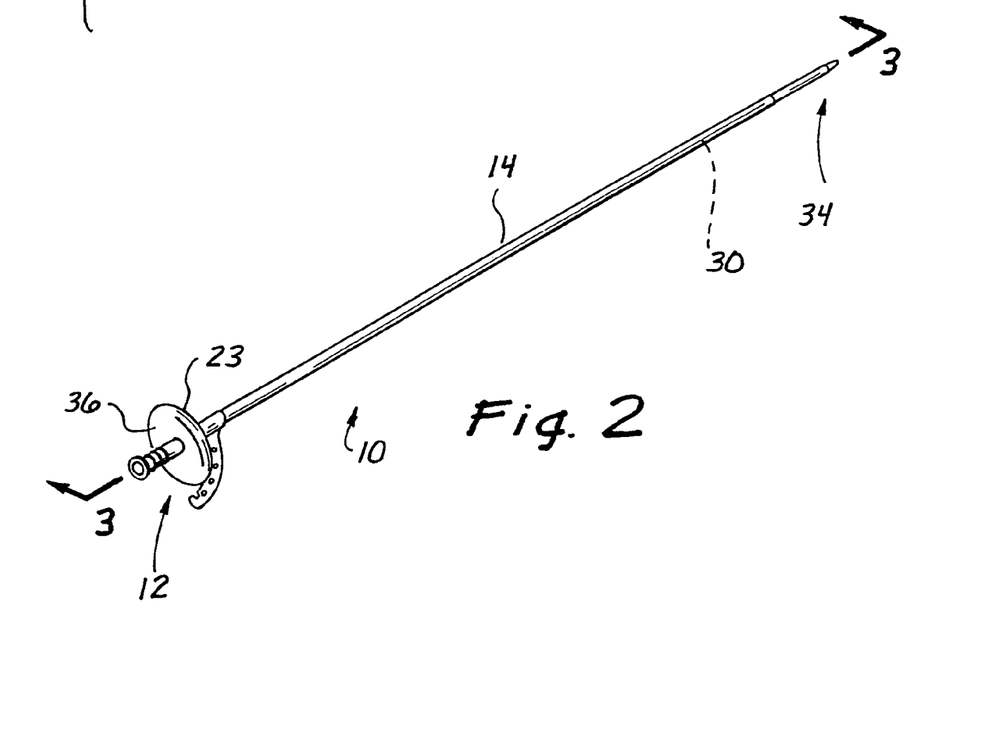
FIG. 2 is a perspective view illustrating the obturator operatively disposed within the sheath.
Figure 3:
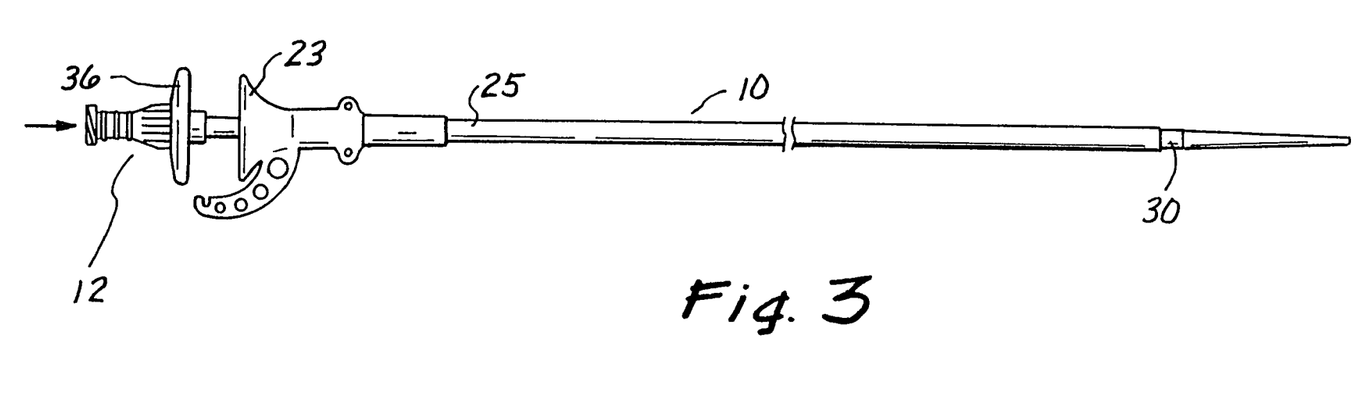
FIG. 3 is a side view illustrating the obturator with a cap operatively disposed within the sheath with the handle.

The obturator 12 will typically have the configuration of an elongate rod 30 extending between a proximal end 32 and a distal end 34. In a preferred embodiment of the invention, a releasable mechanism 36 shaped like a cap is disposed at the proximal end 32 and a tapered tip 38 is formed at the distal end 34. The obturator 12 is adapted to be inserted into the working channel 25 of sheath 10 with the releasable mechanism 36 extending proximally of the sheath 10, and the distal end 34 extending distally of the sheath 10. This operative position of the obturator 12 within the sheath 10 is illustrated in the assembled view of FIG. 2. A side view of the assembled combination is illustrated in FIG. 3. The releasable mechanism 36 is provided to removably attach the obturator 12 to the handle 23 of sheath 10.

Figure 4:
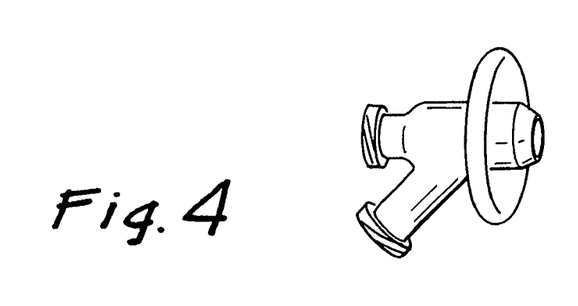
FIG. 4 illustrates another embodiment of a releasable mechanism having multiple openings.

When locked in place with the releasable mechanism 36, the obturator 12 and sheath 10 can then be passed as a single unit over an instrument such as a guidewire. This arrangement precludes inadvertent advancement of the sheath 10 in front of the obturator 12, which could greatly impede proper passage of the sheath through a body cavity such as the ureter. The releasable mechanism 36 is sized and shaped to fit the handle 23. Once the obturator/sheath combination has been advanced to the desired position in the body cavity, the obturator 12 can be removed from the sheath 10 by removing the releasable mechanism 36. Another surgical instrument having a releasable mechanism disposed at its proximal end may then be introduced into the sheath 10, or a separate releasable mechanism may be attached to the handle 23 to prevent passage of fluids or instrumentation. It is appreciated that the releasable mechanism 36 may have different configurations including a snap-on cap as illustrated in FIGS. 1-4, a twist-on cap and any foreseeable releasable mechanism that fits the handle 23 of sheath 10. It is further appreciated that the releasable mechanism may include additional openings such as Luerlock connectors or sidearms providing additional working channels into the sheath as illustrated in FIG. 4.

Another aspect of the invention is the tube 14 may be formed with a spring coil to provide a high degree of kink resistance. As discussed above, there are many advantages to a kink-resistant design of the access sheath such as safety and easy passage of instrumentation. The '304 and '253 patents disclose one such design by reinforcing the elongate tube of the access sheath with a coil. The current methods of fabricating kink-resistant access sheaths, however, are time-consuming, costly and do not provide good yields. Moreover, the fabricated access sheaths do not have a good shelf life. This is because the current manufacturing processes include several challenges. In one example, a current manufacturing process undergoes a dipping process where (1) a mandrel is first dipped in a plastic or PVC material, (2) a wire is then wrapped or wound around the dipped mandrel, and (3) the assembly is then dipped again in the plastic or PVC material multiple times to form the access sheath. While this is a feasible method of producing a kink-resistant access sheath, it is time consuming, costly and produces undesirable yields. The present invention, accordingly, provides alternative methods of manufacturing kink-resistant access sheaths that are more efficient, less costly and provide better yields and improved shelf life.

Figure 5:
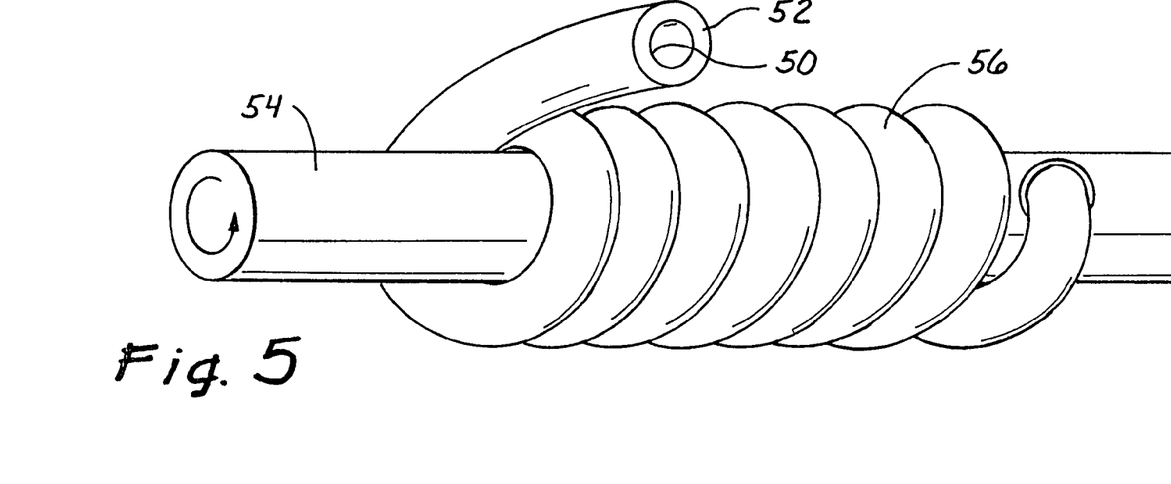
FIG. 5 illustrates a coated wire being wrapped around a mandrel forming a reinforcement spring in a process of manufacturing a kink-resistant sheath in accordance with an embodiment of the invention.
Figure 6:
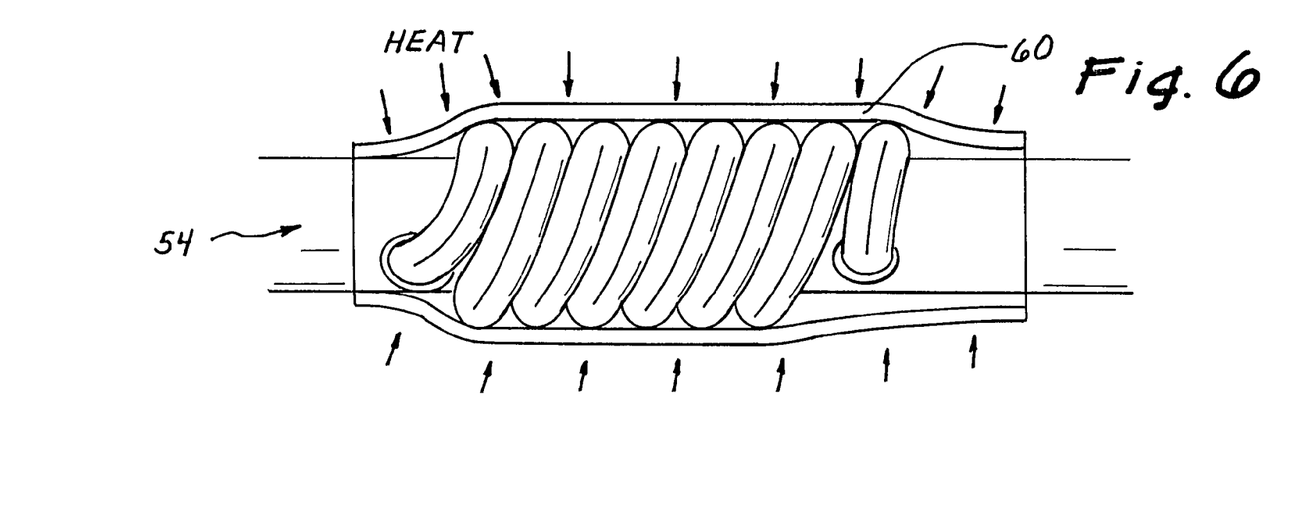
FIG. 6 illustrates the heating process of the wound coated wire using a shrink tube in a process of manufacturing a kink-resistant sheath of the invention.
Figure 7:
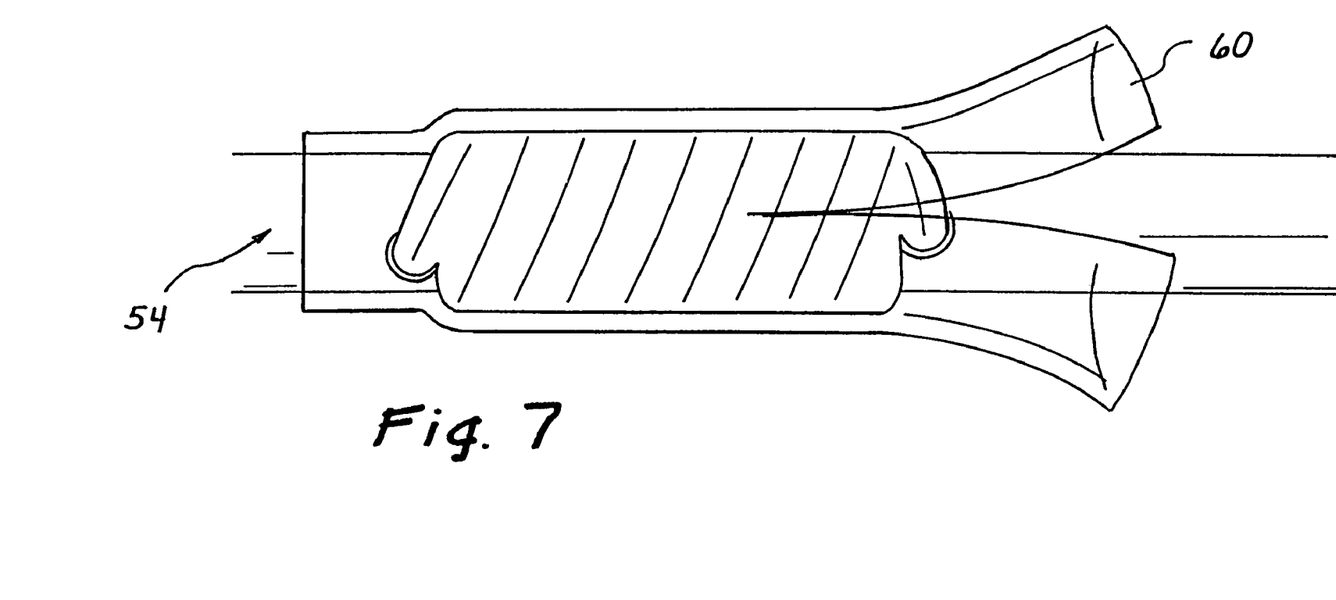
FIG. 7 illustrates the removal of the shrink tube after heating of the wound coated wire in a process of manufacturing a kink-resistant sheath of the invention.

In a first method of the invention as illustrated in FIG. 5, a wire 50 is initially coated with a plastic material 52, e.g., in a coextrusion process; the coated wire 50 is then wrapped or wound on a straight or tapered mandrel 54 forming a desired reinforcement spring 56 (i.e., forming a profile of the resultant tube); after wrapping, the wound coated wire is heated until the plastic material 52 melts and bonds the windings to form the resultant tube or sheath; and once cooled, the sheath is removed from the mandrel 54. It should be noted that the wound coated wire is heated until the plastic material 52 is formed above, below and in between the wire 50. The wire/plastic coextrusion may be round, have straight edges that can be laid adjacent to each other when winding or have interlocking shapes. The wound coated wire may be heated in one of several ways including: (i) capturing the windings within a shrink tube 60 as illustrated in FIG. 6 and heating until the shrink tube 60 encapsulates all the windings and the sheath is formed; and (ii) using a mold to compress the windings and heating the windings until the sheath is formed. The heat shrink tube or mold is then cut or removed from the sheath as illustrated in FIG. 7. That is, after the plastic material such as polyurethane has melted together to form the sheath with spring reinforcement, the shrink tube is cut away and the mandrel is removed.

Figure 9:
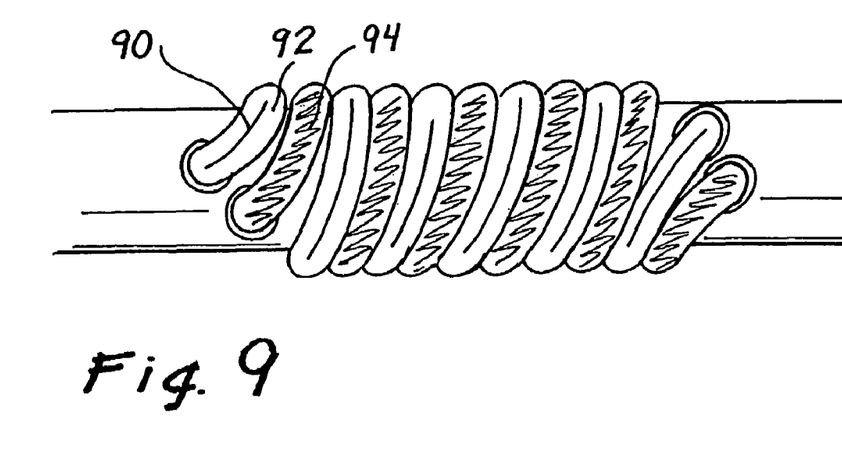
FIG. 9 illustrates a coated wire being alternatively wound around a mandrel with a filament comprising a material different from the coating of the wire.

It is appreciated that the plastic material could be polyurethane, a thermoplastic, a thermoset or any plastic material having hard and/or soft durometer. It is further appreciated that the coated wire could be wound onto the mandrel in a multifilar fashion with materials having alternating durometers as illustrated in FIG. 9. In this embodiment, a wire 90 coated with a more rigid material 92 is alternatively wound with a filament 94 comprising a softer material. The wound coated wire would perform like a spring coil while the softer filament would behave as the more compliant body of the tube allowing kink-resistant bending and twisting. The difference in the durometer of the two materials does not need to be substantial.

Figure 10:
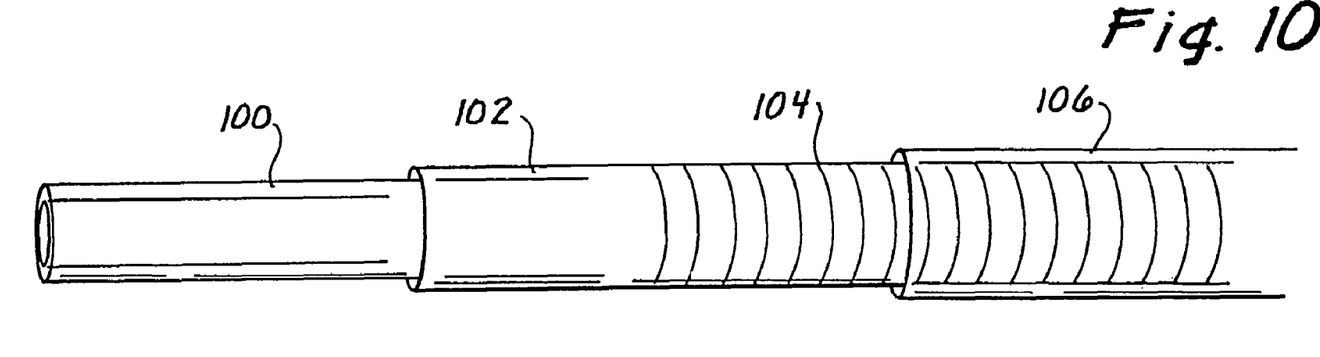
FIG. 10 illustrates a mandrel being used in an extrusion process in accordance with another embodiment of the invention.

In another aspect of the invention as illustrated in FIG. 10, a mandrel 100 is used as part of an extrusion process. In particular, the mandrel 100 is coated with a first layer 102 that would be the resultant internal surface of the tube. A spring reinforcement 104 would then be placed over the first layer 102, and then an outer layer 106 would be extruded over the spring reinforcement 104. An advantage of this embodiment is the resultant tube is not being contoured based on the process itself. As a result, a contoured section could be easily added to an end of the tube providing improved movement of the tube. The addition of the contoured section could be done by either insert-molding, over-molding or melding (fusing) of the contoured section to the tube. It is appreciated that the spring reinforcement 104 could be a pre-wound wire placed around the first layer 102 or a wire wrapped around the first layer 102. It is further appreciated that the gaps between the wires are filled and that the final tube has little or no voids or air bubbles.

Figure 8:
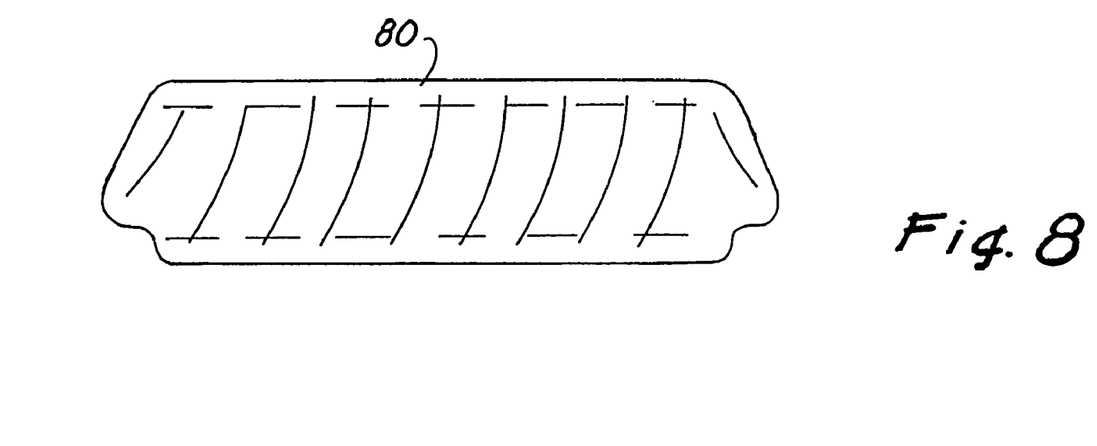
FIG. 8 illustrates a coating of the spring reinforcement in a dipping process in accordance with another embodiment of the invention.

In another embodiment of the invention as illustrated in FIG. 8, another coating or outside layer 80 could be placed over the spring reinforcement by means of a dipping process. In particular, after the mandrel has been coated and the spring reinforcement has been placed or wrapped, the assembly is then dipped in a solvent based solution to form the outer layer 80 onto the tube or sheath. It is appreciated that the final coating could be formed on the resultant tube or sheath using a dipping process either in place of or in addition to the outer layer formed by extrusion. In other words, the final coating could be extruded and/or dipped. It is preferable that the final coating is impervious. An advantage of this embodiment is it allows a layer of a desired material to be formed on the surface of the resultant tube. In yet another embodiment of the invention, a thin flat sheet of polyurethane having a specific width and thickness may be wrapped around the mandrel as a coating. An advantage of this embodiment is it forms an even and smooth coating and it gives some control over the thickness of the coating.

As discussed above, the wire reinforcement could be pre-wound or wound during each of the above processes. Moreover, the material of the wire, the hardness of the wire, the pitch of the windings and the shape of the wire could vary depending on the surgical application of the tube or sheath. For example, the wire may comprise a metallic and/or plastic material. The cross-section of the wire may be round, flat, hexagonal or any other shape that facilitates interlocking of the windings. The use of harder or softer durometer materials is also important as to the inner or outer layer of the tube. Another configuration of the invention uses double reversed springs.

In another aspect of the invention, a braid such as a polyester braid may be used instead of or in addition to the coil spring to form a kink-resistant sheath as generally illustrated in FIGS. 11-15. More particularly, manufacturing a kink-resistant sheath having a braid reinforcement comprises coating a mandrel with a first layer of plastic material to form an inner tube, placing a braid over the inner tube, and coating the braid with a second layer of plastic material to form an outer tube of a braid-reinforced sheath. The braid may comprise of woven fibers made of plastic, metal or any combination of plastics and metals. In one configuration, a spring of length x is placed over a braid having a length of approximately 2 x, the excess braid is then inverted over the spring to form a sheath having two layers of braid surrounding the spring. It is appreciated that the braid may be heat fused to prevent axial stretching. Furthermore, the braid may be insert molded, fused or bonded onto the sheath.

Figure 11:
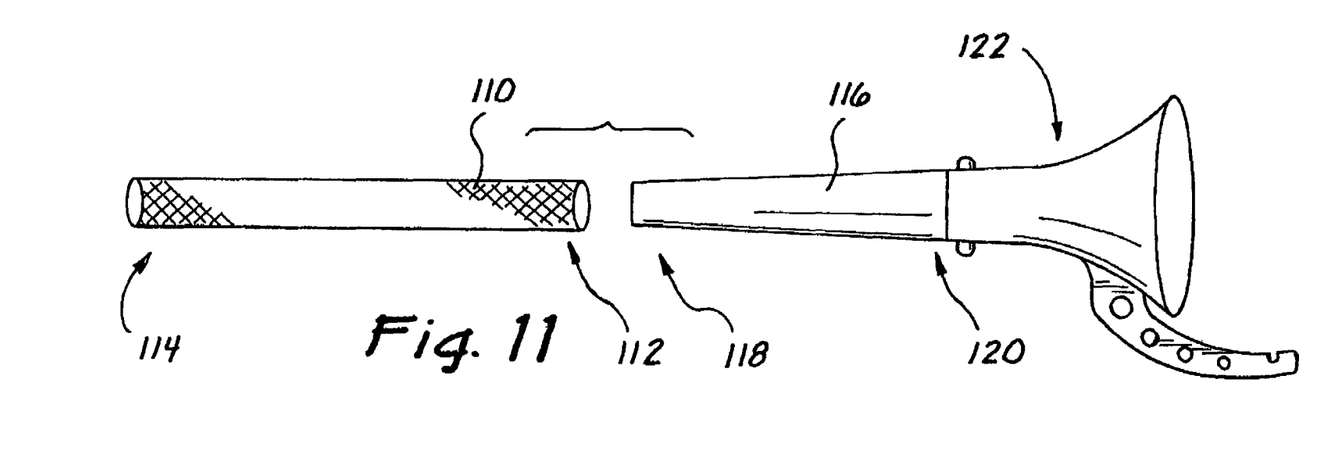
FIG. 11 illustrates a side view of a braid and a tube prior to being fused in accordance with another embodiment of the kink-resistant sheath of the invention.
Figure 12:
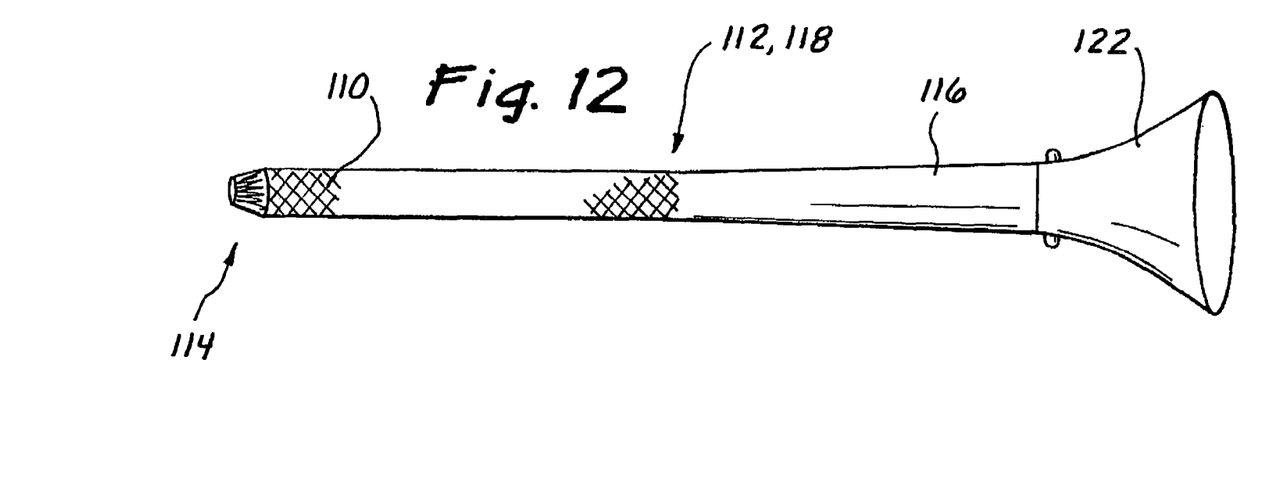
FIG. 12 illustrates fusing of the proximal portion of the braid and the distal portion of the tube.
Figure 13:
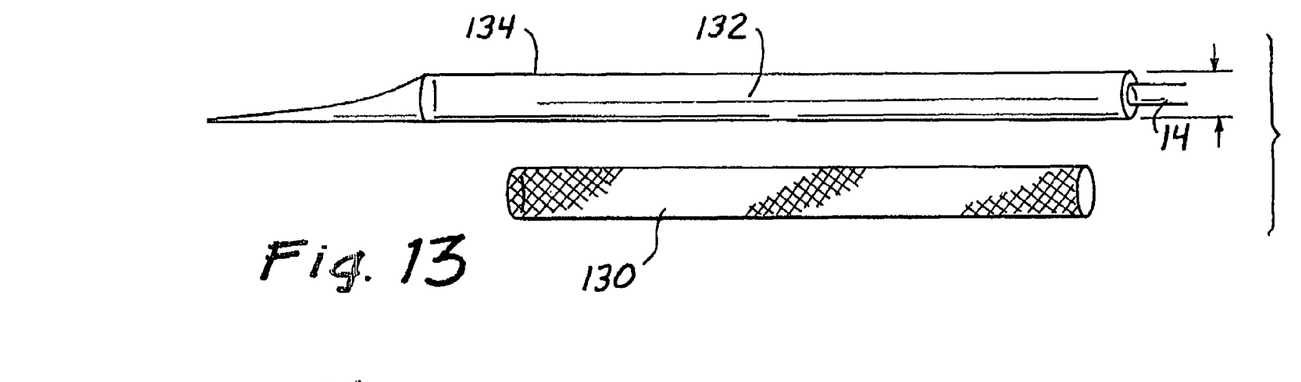
FIG. 13 illustrates a side view of a braid and a tube extruded with a plastic material prior to being fused.
Figure 14:
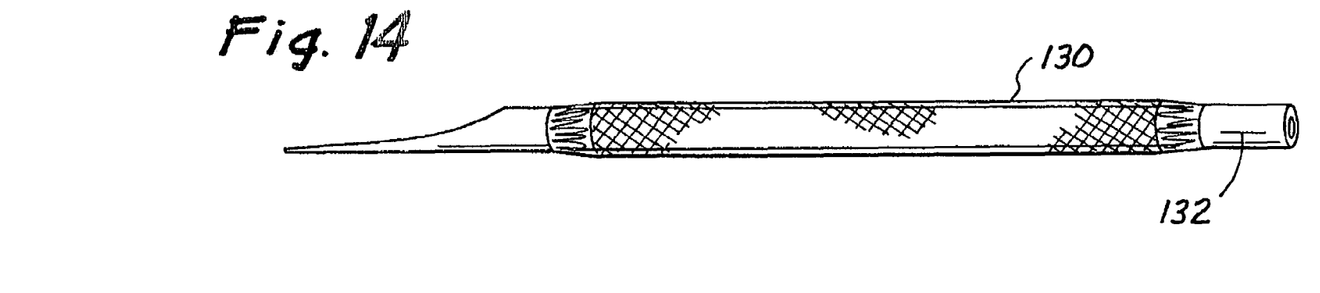
FIG. 14 illustrates fusing of the braid and the tube.
Figure 15:
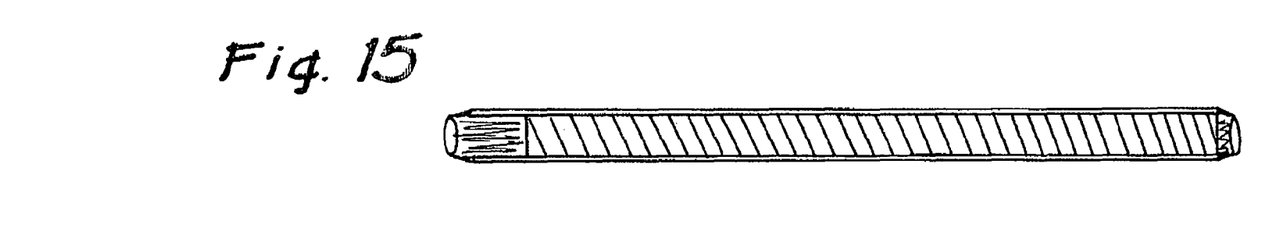
FIG. 15 illustrates a coating of the fused braid and tube with a solvent based solution.

FIG. 11 illustrates an exemplary braid 110 having a proximal portion 112 and a distal portion 114 with a tube 116 having a distal portion 118 and a proximal portion 120 attached to a handle 122. FIG. 12 illustrates the fusing of the proximal portion 112 of braid 110 with the distal portion 118 of tube 116. FIG. 12 further illustrates that the distal portion 114 of braid 110 may be insert or over-molded in a partially deployed condition, fully deployed condition or in a straight condition. FIG. 13 illustrates a braid 130 and a tube 132 extruded with a plastic material 134 prior to fusing. FIG. 14 illustrates the fusing of the braid 130 and tube 132. Finally, FIG. 15 illustrates the coating of the braid 130 and tube 132 with a solvent based solution either by dipping or extrusion.

Although exemplary embodiments of the invention have been shown and described, many other changes, modifications and substitutions will now be apparent to those of ordinary skill in the art, without necessarily departing from the spirit and scope of this invention as set forth in the following claims.

The invention claimed is:

1. A method of manufacturing a kink-resistant sheath, comprising:
   coating a mandrel with a first layer of plastic material to form an inner tube;
   placing a braid over the inner tube;
   placing a spring reinforcement over the braid; and
   coating the braid with a second layer of plastic material to form an outer tube of a braid-reinforced sheath.

2. The method recited in claim 1, wherein placing the braid over the inner tube comprises molding the braid to the inner tube.

3. The method recited in claim 1, wherein placing the braid over the inner tube comprises fusing the braid to the inner tube.

4. The method recited in claim 1, wherein placing the braid over the inner tube comprises bonding the braid to the inner tube.

5. The method recited in claim 1, wherein the spring reinforcement has a length x and the braid has a length of approximately 2 x.

6. The method recited in claim 5, further comprising inverting the excess braid over the spring reinforcement.

7. The method recited in claim 1, wherein the braid is made of polyester.

8. The method recited in claim 1, further comprising heat fusing the braid to prevent axial stretching of the braid.

9. The method recited in claim 1, wherein the braid comprises a plurality of woven fibers made of plastic.

10. The method recited in claim 1, wherein the braid comprises a plurality of woven fibers made of metal.

11. The method recited in claim 1, wherein the braid comprises a plurality of woven fibers made of a combination of plastic and metal.

* * * * *